(12) United States Patent
Werzinger

(10) Patent No.: US 7,340,086 B2
(45) Date of Patent: Mar. 4, 2008

(54) INSPECTION METHOD AND DEVICE

(75) Inventor: Lothar Werzinger, Regensburg (DE)

(73) Assignee: Krones AG, Neutraubling (DE)

( * ) Notice: Subject to any disclaimer, the term of this patent is extended or adjusted under 35 U.S.C. 154(b) by 712 days.

(21) Appl. No.: 10/220,098

(22) PCT Filed: Dec. 15, 2001

(86) PCT No.: PCT/EP01/14848

§ 371 (c)(1),
(2), (4) Date: Aug. 27, 2002

(87) PCT Pub. No.: WO02/054050

PCT Pub. Date: Jul. 11, 2002

(65) Prior Publication Data

US 2003/0012421 A1   Jan. 16, 2003

(30) Foreign Application Priority Data

Dec. 30, 2000   (DE) .................... 100 65 321

(51) Int. Cl.
*G06K 9/00* (2006.01)

(52) U.S. Cl. .................. 382/142; 382/149; 250/223 B; 209/524; 356/239.4

(58) Field of Classification Search ........... 382/149, 382/100, 141, 190, 291, 304, 142; 250/223 R, 250/223 B; 209/522, 523, 524; 356/237.1, 356/239.1, 239.4
See application file for complete search history.

(56) References Cited

U.S. PATENT DOCUMENTS

| | | | |
|---|---|---|---|
| 4,651,879 A * | 3/1987 | Harris et al. ................. | 209/523 |
| 4,924,107 A * | 5/1990 | Tucker ................... | 250/559.46 |
| 5,045,688 A * | 9/1991 | Domenico et al. ....... | 250/223 B |
| 5,067,616 A * | 11/1991 | Plester et al. ................. | 209/3.1 |
| 5,095,204 A * | 3/1992 | Novini .................... | 250/223 B |
| 5,245,399 A | 9/1993 | Wertz et al. | |
| 5,523,560 A * | 6/1996 | Manique et al. ......... | 250/223 B |
| 6,067,155 A * | 5/2000 | Ringlien ................... | 356/240.1 |
| 6,433,338 B1 * | 8/2002 | Nordbryhn et al. ..... | 250/339.12 |
| 6,466,691 B1 | 10/2002 | Heuft | |

FOREIGN PATENT DOCUMENTS

| | | |
|---|---|---|
| DE | 2166235 | 11/1972 |
| DE | 3324449 | 7/1983 |
| DE | 3330817 | 3/1985 |
| DE | 4239203 A1 | 12/1993 |
| DE | 29910452 | 9/1994 |
| DE | 19624552 | 1/1998 |
| DE | 19646678 A1 | 5/1998 |

(Continued)

*Primary Examiner*—Sheela Chawan
(74) *Attorney, Agent, or Firm*—Marshall, Gerstein & Borun LLP

(57) ABSTRACT

An inspection device and a method of checking on correct functioning of the inspection process of containers such as bottles, cans or the like, where a container to be inspected is detected optically at least in part, and the image data thus detected is analyzed with an analysis program to detect defective containers. An especially simple and reproducible function test of the analysis program is made possible by the fact that reference image data is input into the analysis program, this reference image data corresponding structurally to the detected image data and being analyzed by the analysis program with the same parameter settings of the analysis program.

9 Claims, 1 Drawing Sheet

FOREIGN PATENT DOCUMENTS

| | | |
|---|---|---|
| DE | 19646694 | 5/1998 |
| DE | 4302656 | 6/1999 |
| JP | 10-300682 | 11/1998 |
| JP | 11-170489 | 6/1999 |
| JP | 2000-194858 | 7/2000 |

* cited by examiner

INSPECTION METHOD AND DEVICE

FIELD OF THE INVENTION

This invention relates to a method of checking on correct functioning of the inspection process of containers, such as in bottling production lines.

BACKGROUND OF THE INVENTION

Bottling lines usually include (see Unexamined German Patent 196 24 552, for example) inspection systems for empty bottles to be filled. Bottles positioned on a conveyor belt pass through individual inspection devices or modules one after the other to detect certain defects (foreign bodies, residual fluid, damage, material stresses, etc.) in the bottles, so that damaged bottles can be sorted out from the bottling lines.

In particular, the individual inspection modules may each include a camera which records a single image of a glass bottle as it is conveyed past the camera, where the imaging lens of the camera is selected and arranged in such a way that it is also possible to perform an inspection of a side wall or bottom of the container, for example, An image analyzing system connected to such a camera using an image processing program that runs on a computer analyzes the individual image data thus compiled and optionally delivers an error signal to a reject device so that a bottle found to be defective is automatically sorted out from the conveyor belt as a reject.

The image analysis is performed with certain parameter settings of the image analysis program which may be set or altered automatically on manually by an operating person during the analysis or during pauses in the analysis.

These inspection devices may have response characteristics that vary over time, however, so it is necessary to check all functions at certain intervals and optionally perform a suitable readjustment of the individual inspection devices.

Test bottles are usually added either automatically or by hand into the stream of bottles after having been prepared so that they are detected as defective if the inspection modules all function correctly. If these test bottles are not detected as defective, the respective inspection module is faulty, i.e., it is defective or out of adjustment.

This may be due to soiling of the lens or failure of individual components of the electronic detection system or the parameter settings of the image analysis program may be out of adjustment. Such inspection systems are known, for example, from German Utility Model No. 299 10 452.4, which discloses a generic method and a generic device. In this regard, reference is also made to the publications German Patent 196 46 694 A1 and German Patent 43 02 656 C2.

Test bottles may undergo negative changes in their original properties over a period of time due to frequent use. Furthermore, the certainty of detecting test bottles may depend on their random rotational position on the conveyor belt of the inspection machine. The results that can be achieved with the known test bottles are therefore poorly reproducible in principle and are not adequately comparable. These are only simple tests of detected versus not detected which do not allow any qualitative conclusions.

German Patent 2 166 235 and German Patent Application 33 30 817 A1 describe the fact that as an alternative it is not absolutely necessary to introduce prepared test bottles into the path of the beam of the inspection modules, but instead other artificial sources of error may also be introduced in order to check on correct functioning of the inspection process.

However, there is the possibility that in practice the program parameters of the image analysis programs might be partially adjusted in particular by inadequately trained operating personnel, so that the sensitivity of detection of errors is reduced beyond an unacceptable extent. Consequently, there may be cases in which defects in bottles such as abrasion rings in the outer base area of the bottles have a lower probability of being detected, so this reduces the defective bottle reject rate.

SUMMARY OF THE INVENTION

Therefore, the object of the present invention is to make available a method and a device with which it is possible to ascertain easily whether or not the parameter settings of the analyzer program of the inspection device are suitable for a desired probability of error detection, in addition to the basic functional readiness.

In the method according to this invention, which is used for inspection testing of bottles or cans, for example, reference image data is input into the analysis program, this data corresponding structurally to the image data detected and being analyzed by the analysis program at the same parameter settings of the analysis program which are also used for analysis of the image compiled in the process.

In checking on the bottle inspection operation, this thus eliminates the need for first having to insert individual test bottles or other artificial error sources into the series of bottles to be inspected which are conveyed into the path of the beam of the obstacle inspection modules for the inspection.

According to the present invention for example only computer data need be input as reference image data into the analysis program, so this greatly facilitates the possibility of checking on the functioning of the inspection process.

The analysis of whether the existing parameter settings of the analysis program are suitable for achieving the desired result in the inspection operation may be performed much more accurately and precisely with the help of the method according to this invention.

This is due to the fact that it is no longer necessary to take into account in the analysis error sources associated with the settings and adjustment of the optical system protecting the objects to be inspected due to the possibility of direct input of reference image data into the analysis program.

Consequently, an analysis of the instantaneous parameter settings of the analysis program is possible without the instantaneous status of the optical components of the inspection device entering into it as a possible error source.

The method according to this invention also permits more reproducible and comparable results of the function test of the inspection process than was possible with the known processes which involved introducing test bottles into the range of the inspection modules lead in order to check on the current functionality of these modules.

In the case of a side wall inspection, the marks on the test bottles which are to be detected as errors may not be detected by the imaging optical system of the side wall inspection modules because of the rotation of the bottles about their longitudinal axis under some circumstances.

Reference image data is used according to this invention and may consist of, for example, images of test bottles processed previously in which the error marking is correctly discernible, so that such poorly reproducible results cannot occur.

This is thus another important advantage of using reference image data of "fictitious" test bottles, i.e., those that do not actually pass through the inspection device during the function test.

It should be pointed out that although the object of the present invention no longer requires the use of test bottles, it may also be used to advantage when test bottles are still being used for function testing of the optical components of the inspection modules in particular.

The feature that the reference image data should correspond structurally to the image data detected means in the sense of the present patent application that although this reference image data is not image data detected instantaneously by the optical inspection system, it does have a similar data structure so that it may be used just like the detected image data by the analysis program.

The reference image data may include, for example, data from images of test bottles which was recorded with this inspection device under optimum conditions before delivery of the inspection device to the customer.

Accordingly, image data of defective containers is preferably used as the reference image data.

Thus, it should be possible to input image data files into the analysis program representing defective containers, so it is possible despite the fact that test bottles are not actually run through the system, to obtain reliable information regarding suitable parameters settings of the analysis program at the time of the function inspection.

In a preferred embodiment, the reference image data is sent by data transmission for input into the analysis program.

In this case, a remote diagnosis is possible without the person performing the function analysis having to be present directly at the site of the inspection device. Thus, for example, it is possible to monitor inspection equipment set up at various other locations from a central office by data transmission via modem.

The responsible person at the central office may use individual reference image data of images of test bottles having very specific defects, said reference image data being stored in a databank, for example, and this data may be sent by remote data transmission to one of the inspection devices. The data analyzed by the respective analysis program at that location could then be relayed in turn by remote data transmission to the responsible person at the central office for analysis.

Therefore, the personnel expenditure for performing the inspection is greatly reduced in comparison with that of known processes in which in some cases it was still necessary for one person on site to insert test bottles into the row of bottles to be conveyed past the inspection modules.

In addition, it is preferable that the reference image data is prestored in a nonvolatile memory of a computer to which the analysis program then has access in the analysis.

In this case, the reference image data of bottles previously recorded may be stored temporarily on the computer on which the analysis program is also running after this reference image data has been supplied by remote data transmission. The analysis of this reference data need not take place directly after the data is transmitted but instead it may also take place with a time lag, e.g., in a pause in the ongoing inspection process.

As an alternative, the reference image data could also be prestored on the computer with the analysis program at the time of delivery of the respective inspection device to a customer.

The possibility of analysis of the parameter settings and the analysis program which is provided according to this invention and which uses reference image data, making it unnecessary to introduce test bottles or the like on an ongoing basis for the function test may also be used to ascertain and document the suitability of the existing parameter settings.

In an advantageous embodiment, the parameter settings of the analysis program are altered as a function of the result of the analysis of the reference image data.

For example, reference image data may be sent to an inspection device and analyzed not only by remote data transmission and the analyzed data transmitted back again, but also if a suboptimal parameter setting is detected, it may be adjusted automatically in the analysis program or this may in turn be performed by remote data transmission.

In addition, analysis of the reference image data by the analysis program may be performed at least partially or completely at a point in time when the image data detected optically is not being analyzed by the analysis program in order not to interfere with the conventional operating sequence of the ongoing inspection of containers being conveyed past the inspection modules.

The inspection device according to this invention is characterized by a device for input of reference image data into the analysis program, the data corresponding structurally to the image data detected by the measurement unit in order to analyze this data with the analysis program at the same parameter settings which are also used for analysis of the image data detected by the measurement unit.

When the reference image data is prestored in a ROM memory or the computer before delivery of the inspection device to the customer, for example, it is also possible to prevent unintentional deletion of the data.

BRIEF DESCRIPTION OF THE DRAWINGS

This invention is explained and described in greater detail below on the basis of the single accompanying figure, in which.

Figure 1:
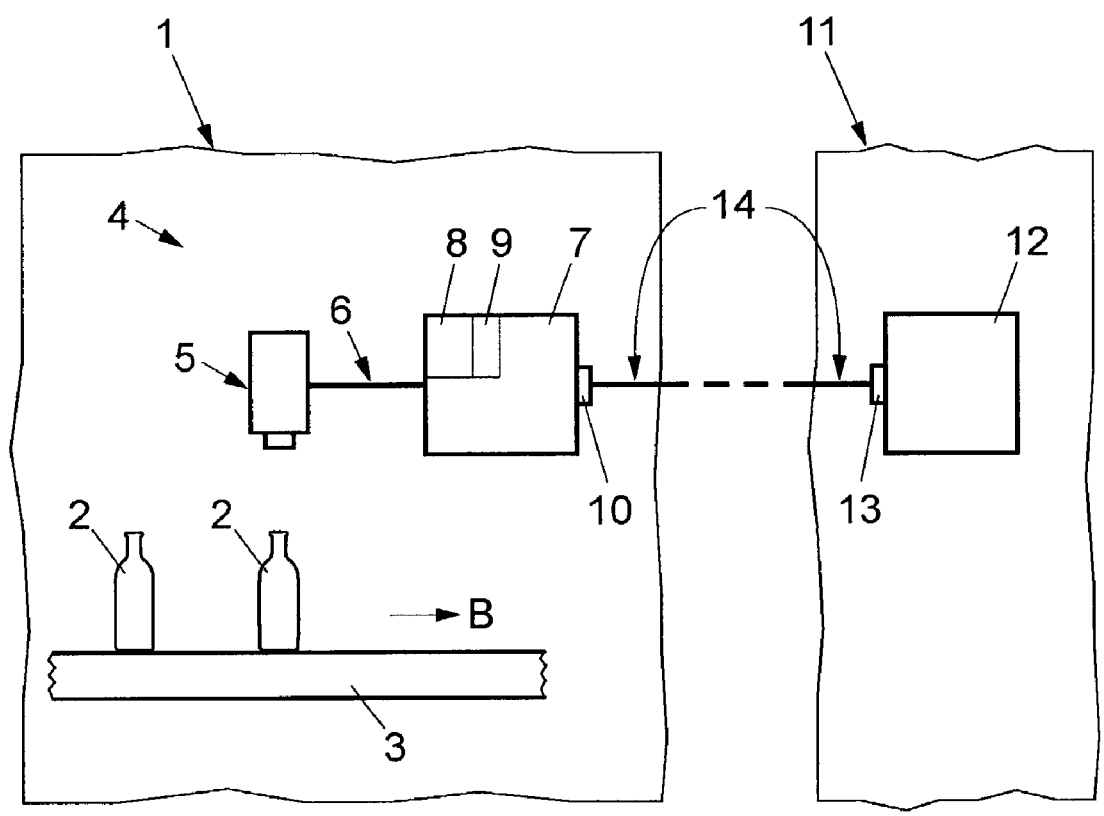
FIG. 1 shows a basic schematic view of an embodiment of an inspection device according to this invention, which may be used for implementing an embodiment of the method according to this invention.

An empty bottle inspection system is located in the area of the factory premises indicated by the outline 1 to detect defective bottles. The bottles 2 are positioned on a running belt 3 and are conveyed in direction B on running belt 3. For the sake of better comprehensibility, only two of the bottles on the running belt are shown here.

An inspection module 4 is set up as an inspection device in the course of running belt 3 so that the bottles 2 conveyed on the running belt 3 each pass through the inspection module 4 individually. The inspection module 4 includes a camera 5 with the respective exposure and imaging optical system to optically record the neck area of the bottles 2 conveyed past it and beneath the module. Of course, the inspection module 5 may be designed and mounted not only for inspection of the neck area but also, for example, as a module for side wall inspection or bottom inspection.

Imaging camera 5 is connected by a signal line 6 in a conventional known manner to an analyzing computer 7 which is shown here schematically. This analyzing computer 7 includes among other things an input keyboard (not shown) in the usual manner and it is connected to a respective monitor for displaying graphics and text.

An image analysis program which is used to analyze the image data detected by camera 5 on the bottles 2 that are inspected is installed on a hard drive 8 or some other data storage device of computer 7. The analysis is usually performed with predetermined and variable parameter settings of the analysis program. In addition to the hard drive 8, computer 7 also includes a ROM memory 9 in which reference image data are stored in a nonerasable form.

In addition, analyzing computer 7 includes a connection having an interface 10. This is used for input of reference image data, among other things, into the writable memory of computer 7 via remote data transmission so that this data can be analyzed by the analysis program immediately or after a certain period of time.

In this regard, another computer 12 may also be present at a different location (e.g., at the office of the manufacturer of the machine), as symbolized schematically by bordering line 11. This computer 12 also includes, for example, a connection to interface 13 for remote data transmission. The two computers 7 and 12 at the different locations 1, 11 are connectable by a line 14 indicated schematically, e.g., a modem connection 14 to transmit data from computer 12 to computer 7 and vice versa.

With the help of a device illustrated in the FIG., the method according to this invention may be carried out as described below.

For example, when installing the inspection device 4 in the respective manufacturing building with the empty bottle belt conveyor 3, images of test objects such as test bottles are recorded with the help of camera 5 and the connected analyzing computer 7 by the personnel responsible for installation of the device 4. This data has been stored in ROM memory 9 as reference image data in a non-rewritable form. As an alternative, data may also be stored on the hard drive 8.

After this installation and storage of reference image data in a nonvolatile memory of computer 7, the inspection device may finally be started for operation in the factory building at site 1.

The inspection process itself takes place in an essentially known manner, in that bottles 2 are transported on the running belt 3 in the direction B of conveyance to inspection module 4 for inspection of the neck area of the bottles 2. The bottles are guided individually into the imaging area of recording camera 5 of module 4 and a single image of the bottle 2 which is instantaneously in that location is recorded.

Then digital image data of the image thus recorded is generated by camera 5 in the inspection module 4 and sent to the image analyzing computer 7 by means of the connecting line 6. The digital image data thus transmitted is then analyzed by the analysis program stored in computer 7 at given parameter settings in order to detect defective containers. The parameter settings may be either determined in advance by an operating person or they may be adjusted by an operating person during the analysis process or between different analysis runs in order to optimize the analysis.

During a period of time in which none of the digital image data detected by camera 5 is analyzed by the analysis program, the reference image data stored in advance in memory 8 or 9 may be entered into the analysis program running on computer 7, e.g., routinely at certain intervals or at a certain point in time with the data entry performed by an operating person.

The reference image data thus inputted is then analyzed in the analysis program at the same parameter settings which are also used for analysis of the image data thus detected. In other words, the reference image data is on "imaginary" test bottles which are not actually present on the conveyor belt 3 in the area of inspection modules 4 during the ongoing function test. Data thus inputted is then analyzed by the analysis program with the same parameter settings which are also used for analysis of the image data detected by camera 5. This process may also take place fully automatically in inspection operations or at longer intervals of time between recording the images of successive bottles.

This analysis of reference image data is thus performed, for example, by using as the basis the parameter sets of the analysis program used for the last inspection process with the analysis of the image data detected most recently by camera 5.

Depending on the result of this analysis of the reference image data, for example, the operating person may be determine whether the parameters of the program deviate too greatly in an unwanted manner from the range required for a precise and accurate analysis as desired. It would also be conceivable for the parameter settings of the analysis program to be subsequently altered automatically until the analysis of the reference image data input at the moment yields a desired result.

Although the case has already been described wherein the reference image data was already stored in memory 8, 9 of computer 7 before performing the actual inspection process and the respective function tests of this process, the following case would also be conceivable as an alternative or in addition.

At any desired point in time, a person at site 11 which is thus not in the area of the factory on site 1, could transfer by remote data transmission from computer 12 the reference image data to computer 7 for subsequent analysis, this data transfer being accomplished by means of remote data transmission devices, i.e., interfaces 10, 13 and modem connecting line 14.

As in the present case, this reference image data could be either data from test bottles recorded previously with the inspection module or as an alternative this reference image data could also have other features which could be used for testing the analysis program for proper functioning.

In other words, the respective reference need not necessarily be an image of a test bottle per se, but instead other objects could also be used or computer generated graphics could be used as reference image data having certain brightness distributions, for example, which are useful for detecting defective parameter settings in the analysis program.

The device according to this invention and the method according to this invention consequently make it possible to check for proper functioning of the analysis program of the inspection system in a simple, reliable and reproducible manner.

The invention claimed is:

1. A method of checking on correct functioning of the inspection of containers (2) such as bottles, cans or the like, to be optically tested, comprising the steps of optically detecting the image data of a container (2) at least in part, analyzing the image data thus compiled with an analysis program to detect defective containers, inputting reference image data into the analysis program, using image data from defective containers as the reference image data, and causing the reference image data to correspond structurally to the image data compiled and to be analyzed by the analysis program at the same parameter settings of the analysis program which is also used for analyzing the image data thus detected.

2. The method according to claim 1, further comprising sending the reference image data to the analysis program by remote data transmission for input into the program.

3. The method according to claim 1, further comprising storing the reference image data in advance in a nonvolatile memory (8, 9) of a computer (7) which is accessed by the analysis program in performing the analysis.

4. The method according to claim 1, further comprising altering the parameter settings of the analysis program as a function of the results of the analysis of the reference image data.

5. The method according to claim 1, further comprising performing the analysis of the reference image data by the analysis program entirely or at least in part when the optically detected image data is not being analyzed by the analysis program.

6. An inspection device (4) for containers (2) such as bottles, cans or the like, comprising a measuring unit (5) for optical detection of at least a part of the container (2) to be tested, a computer assisted analysis system (7) having an analysis program for analyzing the image data detected by the measuring unit (5) in order to detect defective containers, and a device for input of reference image data into the analysis program, wherein the reference image data corresponds structurally to the image data detected by the measuring unit (5) and includes image data from defective containers, in order to analyze the reference image data with the analysis program at the same parameter settings which are also used for analysis of the image data detected by the measuring unit (5).

7. The inspection device according to claim 6, wherein the reference image data is stored in advance in a nonvolatile memory (8, 9) of a computer (7) of the computer assisted analysis program (7).

8. The inspection device according to claim 7, wherein the reference image data is stored in advance in a ROM memory (9) of the computer (8, 9).

9. The inspection device according to claim 6, wherein the computer assisted analysis system (7) includes as the device for input of reference image data a connection (10) for input of reference image data by remote data transmission.

* * * * *

UNITED STATES PATENT AND TRADEMARK OFFICE
CERTIFICATE OF CORRECTION

| | | |
|---|---|---|
| PATENT NO. | : 7,340,086 B2 | |
| APPLICATION NO. | : 10/220098 | |
| DATED | : March 4, 2008 | |
| INVENTOR(S) | : Lothar Werzinger | |

It is certified that error appears in the above-identified patent and that said Letters Patent is hereby corrected as shown below:

<u>TITLE PG</u>,

Item (30), "100 65 321" should be -- 100 65 321.9 --.

Signed and Sealed this

Twelfth Day of August, 2008

JON W. DUDAS
*Director of the United States Patent and Trademark Office*